United States Patent
Lazic

(10) Patent No.: US 11,147,565 B2
(45) Date of Patent: Oct. 19, 2021

(54) SURGICAL CLIP WITH BEARING SLEEVE

(71) Applicant: Lazic Besitz GmbH & Co. KG, Tuttlingen (DE)

(72) Inventor: Daniel Lazic, Tuttlingen (DE)

(73) Assignee: LAZIC BESITZ GMBH & CO KG, Tuttlingen (DE)

( * ) Notice: Subject to any disclaimer, the term of this patent is extended or adjusted under 35 U.S.C. 154(b) by 187 days.

(21) Appl. No.: 16/140,517

(22) Filed: Sep. 24, 2018

(65) Prior Publication Data
US 2019/0090881 A1 Mar. 28, 2019

(30) Foreign Application Priority Data
Sep. 28, 2017 (EP) ..................................... 17193619

(51) Int. Cl.
*A61B 17/122* (2006.01)
*A61B 17/12* (2006.01)

(52) U.S. Cl.
CPC ..... *A61B 17/1227* (2013.01); *A61B 17/12113* (2013.01)

(58) Field of Classification Search
CPC ........ A61B 17/1227; A61B 2017/0092; A61B 17/1222; A61B 17/08; A61B 17/122; A61B 17/128; A61B 17/1285; A61B 17/083; A61B 2017/081; Y10T 24/4447
See application file for complete search history.

(56) References Cited

U.S. PATENT DOCUMENTS

| 4,932,955 | A | | 6/1990 | Merz | |
|---|---|---|---|---|---|
| 5,925,064 | A | * | 7/1999 | Meyers | A61B 17/3201 606/205 |
| 9,386,987 | B2 | * | 7/2016 | Lazic | A61B 17/1227 |
| 9,585,673 | B2 | * | 3/2017 | Zieris | A61B 17/1227 |
| 2014/0194908 | A1 | * | 7/2014 | Lazic | A61B 17/083 606/151 |
| 2015/0289876 | A1 | | 10/2015 | Lazic | |
| 2016/0157867 | A1 | * | 6/2016 | Zieris | A61B 17/1227 606/158 |

FOREIGN PATENT DOCUMENTS

| DE | 35 23 031 A1 | 1/1986 |
|---|---|---|
| DE | 103 09 491 A1 | 9/2004 |
| EP | 2 752 164 A1 | 7/2014 |
| EP | 2 929 843 A1 | 10/2015 |

* cited by examiner

*Primary Examiner* — Katherine H Schwiker
*Assistant Examiner* — Raihan R Khandker
(74) *Attorney, Agent, or Firm* — Hackler Daghighian Martino & Novak

(57) ABSTRACT

A surgical clip includes two clip parts that are rotatably interconnected by a separate bearing sleeve, and a leg spring which pretensions the two clip parts to an initial rotary position. The coil body of said leg spring is at least partially being disposed within the bearing sleeve, wherein the bearing sleeve is disposed so as to be non-rotatable in an opening of the one first of the two clip parts and is disposed so as to be rotatable in an opening of the other, second clip part. The first of the two spring legs of the leg spring is supported on the bearing sleeve, and the other, second spring leg is supported on the second clip part. The bearing sleeve has an axially protruding protrusion on which the first spring leg is supported.

19 Claims, 5 Drawing Sheets

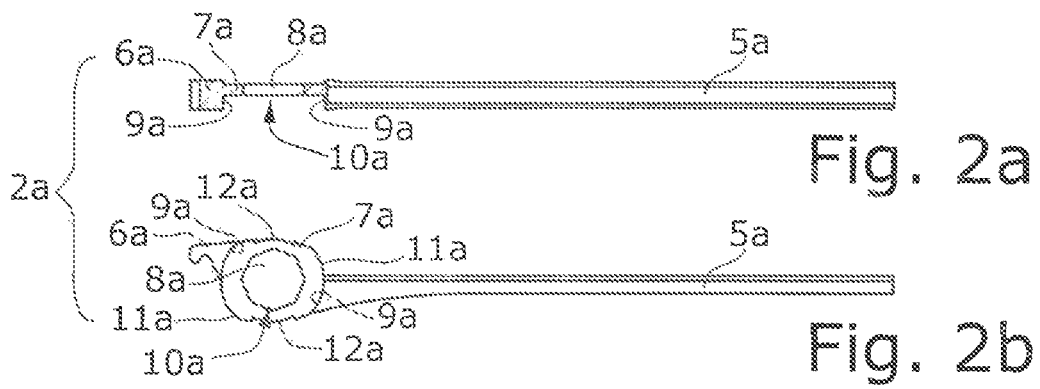
Fig. 2a
Fig. 2b
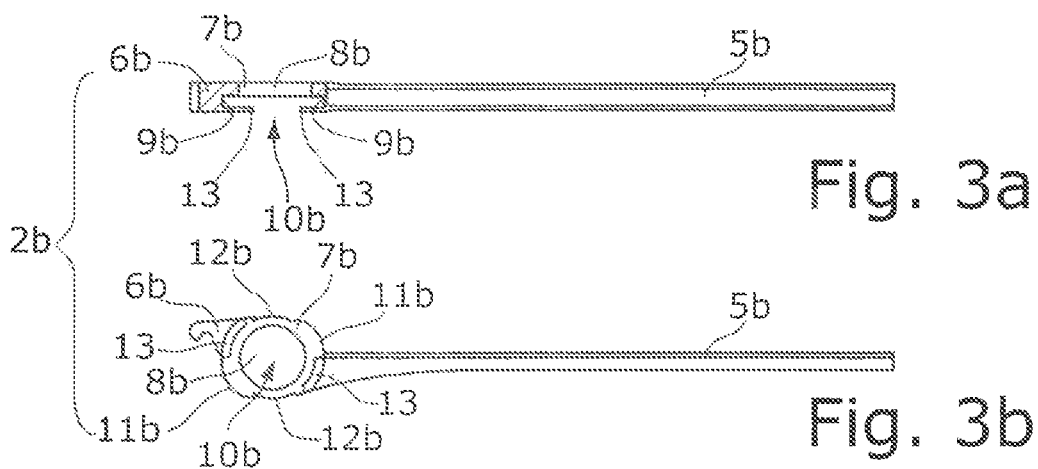
Fig. 3a
Fig. 3b
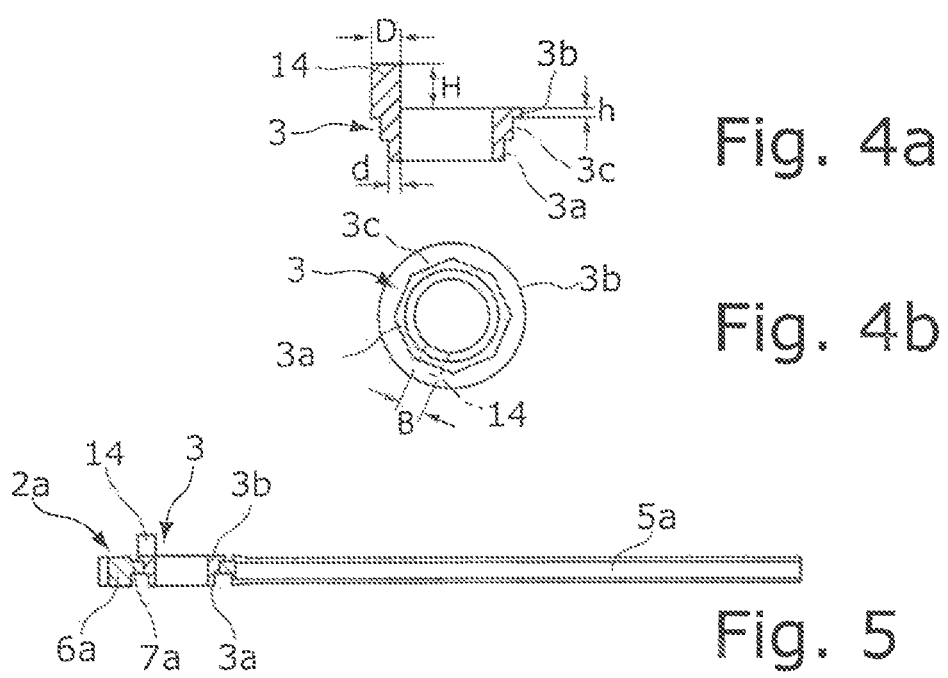
Fig. 4a
Fig. 4b
Fig. 5

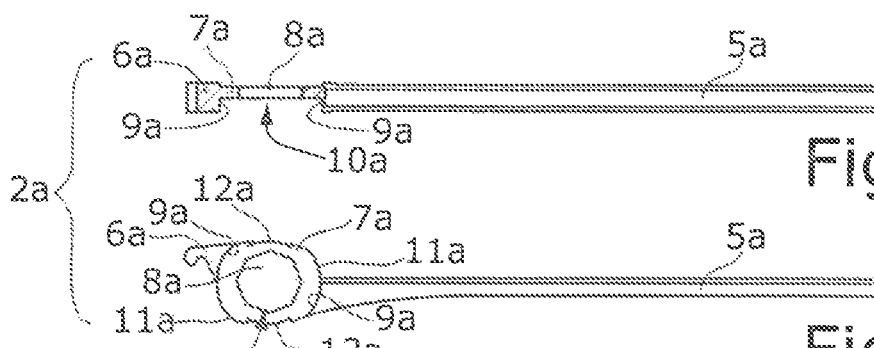
Fig. 7a
Fig. 7b
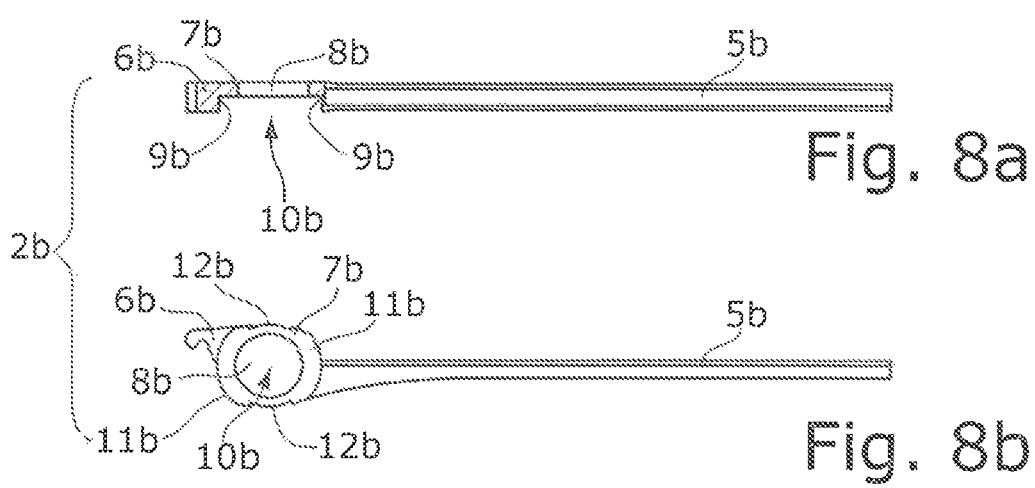
Fig. 8a
Fig. 8b
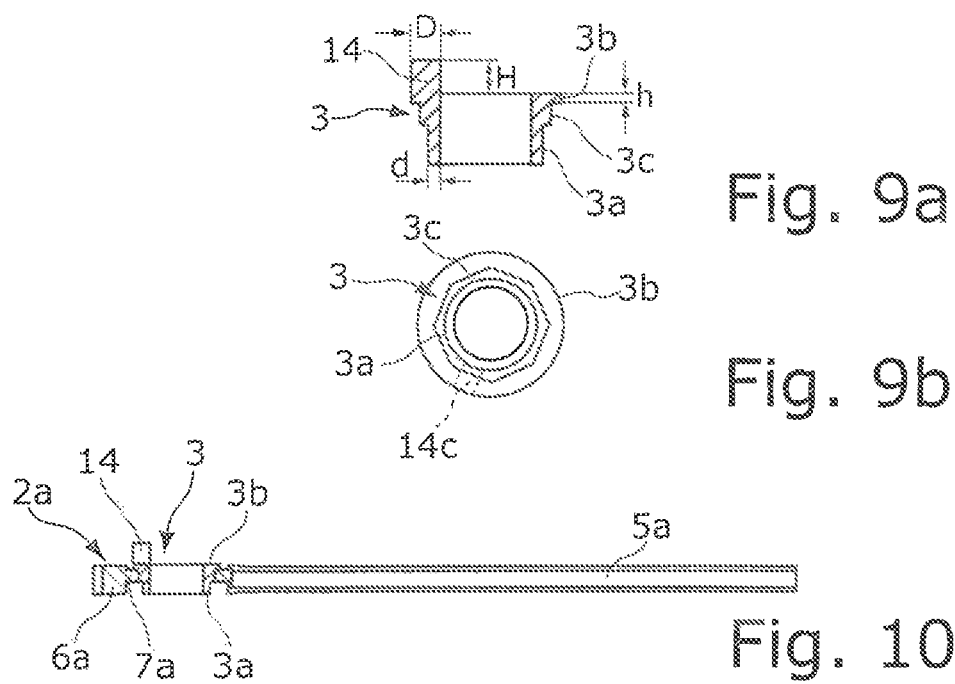
Fig. 9a
Fig. 9b
Fig. 10

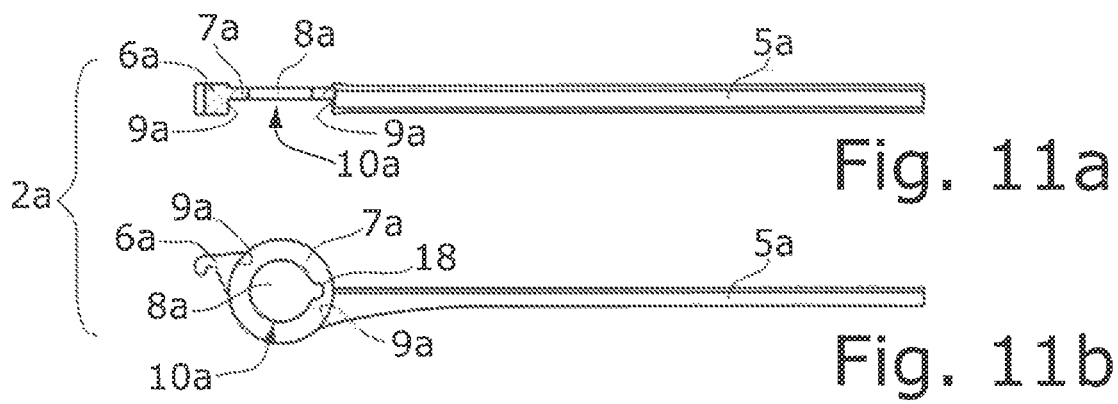
Fig. 11a
Fig. 11b
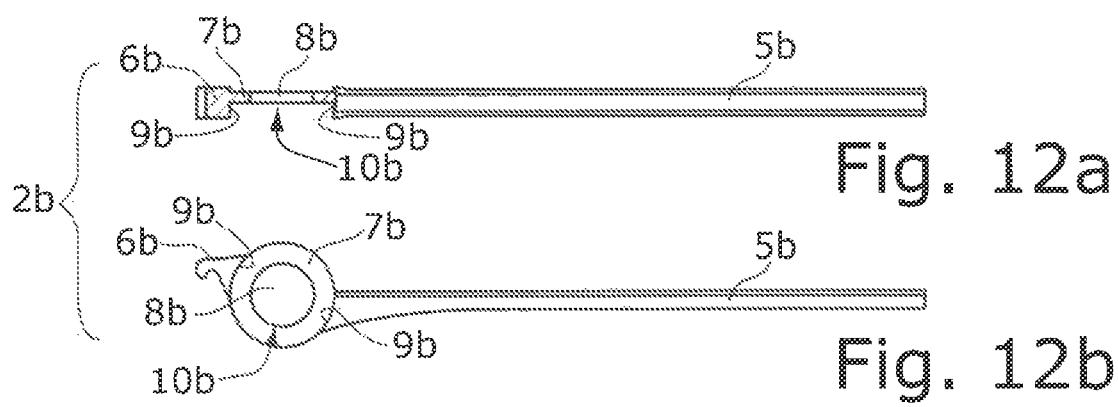
Fig. 12a
Fig. 12b
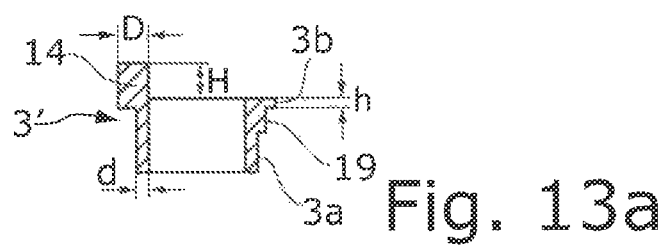
Fig. 13a
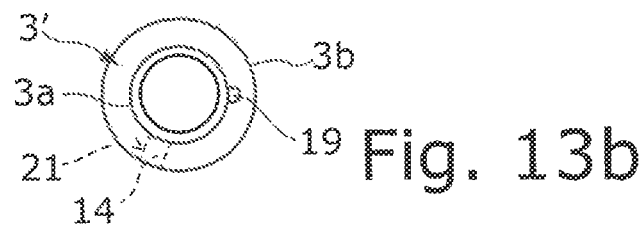
Fig. 13b
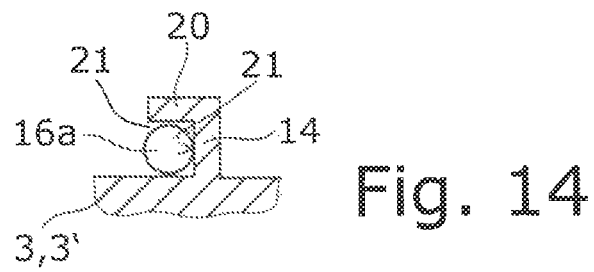
Fig. 14

SURGICAL CLIP WITH BEARING SLEEVE

CROSS-REFERENCE TO RELATED APPLICATIONS

This application claims priority to European Patent Application No. 17 193 619.8 filed on Sep. 28, 2017, the entire contents of which are hereby incorporated in full by this reference.

DESCRIPTION

Field of the Invention

The invention relates to a surgical clip, in particular an aneurysm clip, comprising two clip parts that are rotatably interconnected by means of a separate bearing sleeve, and a leg spring which pretensions the two clip parts to an initial rotary position, the coil body of said leg spring at least partially being disposed within the bearing sleeve, wherein the bearing sleeve is disposed so as to be non-rotatable in an opening of a first of the two clip parts and is disposed so as to be rotatable in an opening of the other, second clip part, and wherein a first of the two spring legs of the leg spring is supported on the bearing sleeve, and the other, second spring leg is supported on the second clip part.

Background of the Invention

A surgical clip of this type has become known, for example, by way of EP 2 752 164 A1. This known clip has a separate thin bearing sleeve from metal (for example titanium), which is plug-fitted in a non-rotatable manner into an opening of the first clip part and on which the second clip part by way of the opening thereof is rotatably mounted. The bearing sleeve thus forms the rotary mounting about which the second clip part rotates. The bearing sleeve has a plug stop in the form of an encircling thin outer edge to which the one spring leg of the leg spring is welded, specifically advantageously prior to plug-fitting the bearing sleeve into the first clip part. However, in the welding of the spring leg there is the risk of the thin outer edge being damaged or even destroyed, and of the bearing sleeve in this instance having to be discharged as a reject part, on account of which the production costs and the assembly complexity are significantly increased.

SUMMARY OF THE INVENTION

By contrast, it is the object of the present invention to improve the support or fastening, respectively, of the one spring leg on to the bearing sleeve in the case of a surgical clip of the type mentioned at the outset.

This object is achieved according to the invention in that the bearing sleeve has a protrusion which protrudes axially beyond the one sleeve end side of said bearing sleeve, the first spring leg being supported on said protrusion in the force direction of the leg spring.

The bearing sleeve thus has, according to the invention, a protrusion on which the leg spring by way of one spring leg thereof is supported. This spring leg bearing thereon can additionally be welded, ultrasonically welded, adhesively bonded, or soldered to the protrusion. In the case of a bearing sleeve from plastics material, the spring leg bearing thereon can also be at least partially embedded in a form-fitting manner, in particular insert moulded, in the protrusion and be fixed therein on account thereof.

The axial height of the protrusion is preferably larger than the diameter of the first spring leg in order for the first spring leg to reliably bear on the protrusion. The protrusion can also be configured so as to be hook-shaped, in order to be able to hook the first spring leg onto said protrusion and to thus be able to axially fix the first spring leg on the protrusion.

The radial thickness of the protrusion is particularly preferably larger than the wall thickness of the bearing portion of the bearing sleeve on which the second clip part is rotatably mounted. On account thereof, the protrusion is configured so as to be more solid than the bearing portion of the bearing sleeve and can be welded to the spring leg bearing thereon without damage.

The protrusion most particularly preferably protrude axially on an encircling outer edge of the bearing sleeve. The axial height of the protrusion herein is advantageously larger than the height of the outer edge such that the spring leg bearing thereon can be welded to the protrusion without the outer edge being damaged herein. In particular in the case of a bearing sleeve from plastics material, the spring leg bearing thereon can at least partially be melted into the protrusion without the actual bearing sleeve being damaged by the heat arising hereby. That sleeve end that is opposite the outer edge is preferably bent back so as to form a rivet head, such that the two clip parts are held together on the bearing sleeve between the outer edge and the rivet head.

The second spring leg can likewise be welded, adhesively bonded, or soldered to the second clip part, or else be hooked onto the second clip part, which is preferable, or simply encompass the second clip part in a manner similar to that of a clothes peg.

The bearing sleeve and/or the leg spring are/is preferably formed from a metal, in particular titanium. Particularly preferably, the two clip parts are formed from an X-ray-transparent plastics material, in particular PEEK (polyether ether ketone).

Further advantages of the invention are derived from the description, the claims, and the drawing. The features mentioned above and set forth hereunder can likewise be used individually or in pluralities thereof in arbitrary combinations. The embodiments shown and described are not to be understood as an exhaustive enumeration but rather have an exemplary character in order for the invention to be visualized.

BRIEF DESCRIPTION OF THE DRAWINGS

In the drawings:

FIGS. 2a, 2b show a first clip part shown in FIG. 1 in a sectional view (FIG. 2a) and in a plan view of the clip-part internal side (FIG. 2b);

FIGS. 3a, 3b show the other, second clip part shown in FIG. 1 in a sectional view (FIG. 3a) and in a plan view of the clip-part internal side (FIG. 3b);

FIGS. 4a, 4b show the bearing sleeve shown in FIG. 1 in a sectional view (FIG. 4a) and in a plan view (FIG. 4b);

FIG. 5 shows the first clip part shown in FIG. 2, having the bearing sleeve plug-fitted thereinto in a non-rotatable manner, in a sectional view analogous to that of FIG. 2a;

FIGS. 7a, 7b show a first clip part shown in FIG. 6 in a sectional view (FIG. 7a) and in a plan view of the clip-part internal side (FIG. 7b);

FIGS. 8a, 8b show the other, second clip part shown in FIG. 6, in a side view (FIG. 8a) and in a plan view of the clip-part internal side (FIG. 8b);

FIGS. 9a, 9b show the bearing sleeve shown in FIG. 6 in a sectional view (FIG. 9a) and in a plan view (FIG. 9b);

FIG. 10 shows the first clip part shown in FIG. 7, having the bearing sleeve plug-fitted thereinto in a non-rotatable manner, in a sectional view analogous to that of FIG. 7a;

FIGS. 11a, 11b show the first clip part of a third embodiment of the clip according to the invention in a sectional view (FIG. 11a) and in a plan view of the clip-part internal side (FIG. 11b);

FIGS. 12a, 12b show the second clip part of the third embodiment in a side view (FIG. 12a) and in a plan view of the clip-part internal side (FIG. 12b);

FIGS. 13a, 13b show the bearing sleeve of the third embodiment in a sectional view (FIG. 13a) and in a plan view (FIG. 13b); and FIG. 14 shows a modification of a protrusion of the clip according to the invention.

DETAILED DESCRIPTION OF THE PREFERRED EMBODIMENTS

In the following description of the drawings, identical reference signs are used for the same or functionally equivalent components, respectively.

Figure 1A:
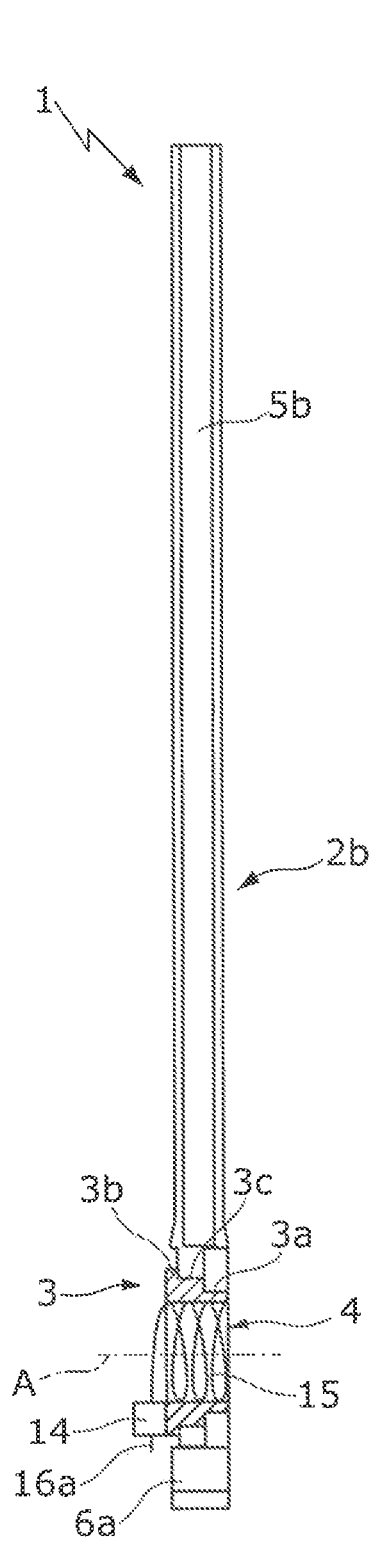
FIGS. 1a, 1b show a first embodiment of the clip according to the invention, said clip being plugged together from two clip parts and one bearing sleeve, in a closed initial rotary position, in a sectional view (FIG. 1a) and a plan view (FIG. 1b)
Figure 1B:
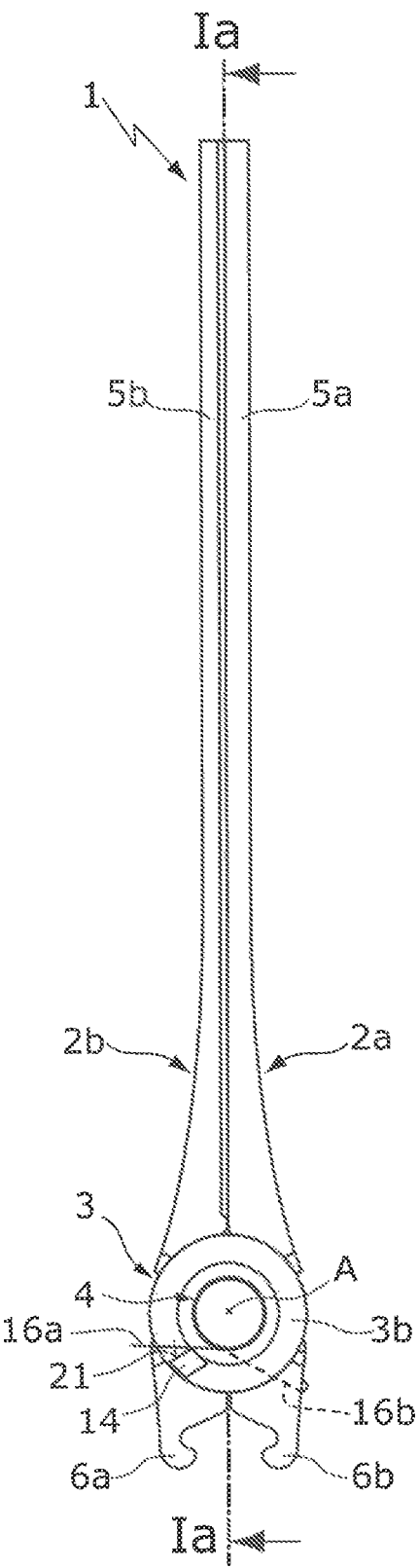

The aneurysm clip 1 shown in FIGS. 1a, 1b comprises two double-arm clip parts 2a, 2b, a bearing sleeve 3 which mounts the two clip parts 2a, 2b so as to be rotatable about the sleeve axis A, and a leg spring 4 which pretensions the two clip parts 2a, 2b to the closed initial rotary position shown.

The two clip parts 2a, 2b have each one long clamping arm 5a, 5b and one short operating arm 6a, 6b which in relation to the rotation axis A are mutually opposite and mutually offset in a parallel manner. The operating arms 6a, 6b with the aid of a applying forceps that engage between the two operating arms 6a, 6b can be forced apart counter to the closing force of the leg spring 4, and the clamping arms 5a, 5b can be opened on account thereof.

As is shown in FIGS. 2a, 2b, the one, first clip part 2a between the clamping arm 5a and the operating arm 6a has a flat annular portion (middle portion) 7a having an octagonal opening 8a. The annular portion 7a in relation to the clamping arm 5a and the operating arm 6a is set back in an axial manner by way of two partially cylindrical shoulders 9a, so as, on account thereof, to form an axially open plug receptacle 10a. The annular portion 7a forms the base, or the base plate, respectively, of the plug receptacle 10a, and the two shoulders 9a form two side walls of the plug receptacle 10a which in relation to the opening 8a are mutually opposite. The annular portion 7a has two first annular segments 11a which in relation to the opening 8a are mutually opposite, and therebetween in each case one second annular segment 12a, wherein the second annular segments 12a on the outer side in relation to the first annular segments 11a are each set back in a radial manner towards the inside.

As is shown in FIGS. 3a, 3b, the other, second clip part 2b between the clamping arm 5b and the operating arm 6b likewise has a flat annular portion (middle portion) 7b having a circular opening 8b. The annular portion 7b in relation to the clamping arm 5b and the operating arm 6b is set back in an axial manner by way of two partially cylindrical shoulders 9b so as to, on account thereof, form an axially open plug receptacle 10b. The annular portion 7b forms the base, or the base plate, respectively, of the plug receptacle 10b, and the two shoulders 9b form two side walls of the plug receptacle 10b that in relation to the opening 8b are mutually opposite. The annular portion 7b has two first annular segments 11b which in relation to the opening 8b are mutually opposite, and therebetween in each case one second annular segment 12b, wherein the two annular segments 12b on the outer side in relation to the first annular segments 11b are each set back in a radial manner towards the inside. The two shoulders 9b on the side that is opposite the base plate 7b are each overreached by a projection 13 and, on account thereof, are configured as circumferential grooves. The second clip part 2b, with the exception of the two projections 13 thereof, can be configured in a manner identical to that of the first clip part 2a. While the second annular segments 12b are not required for functional reasons, said second annular segments 12b however enable the two clip parts 2a, 2b to be made from the same blanks.

The bearing sleeve 3 shown in FIGS. 4a, 4b at one end has a bearing portion 3a having a circular external cross section, at the other end an encircling annular collar, or outer edge 3b, respectively, and therebetween an octagonal plug portion 3c. The plug portion 3c in relation to the outer edge 3b is set back in a radial manner towards the inside, and the bearing portion 3a in relation to the plug portion 3c is set back in a radial manner towards the inside. Furthermore, the bearing sleeve 3 has a protrusion 14 that projects axially beyond the outer edge 3b, the radial thickness D of said protrusion 14 being larger than the wall thickness d of the bearing portion 3a, and the axial height H of said protrusion 14 being larger than the height h of the outer edge 3b. The width B of the protrusion 14 in the circumferential direction of the sleeve is likewise in each case larger than the wall thickness d of the bearing portion 3a and the height h of the outer edge 3b.

The bearing sleeve 3 by way of the octagonal plug portion 3c in FIG. 5 is plug-fitted into the octagonal opening 8a of the first clip part 2a and is thus held so as to be non-rotatable therein. The bearing sleeve 3 by way of the outer edge 3b thereof bears on the outside on the annular portion 7a of the first clip part 2a, and by way of the circular bearing portion 3a of said bearing sleeve 3 projects beyond the annular portion 7a on the inside. Instead of being octagonal as shown, the opening 8a and the plug portion 3c can also have any other non-circular cross section, for example another polygonal cross section or an oval cross section.

In order for the clip 1 to be assembled, the first clip part 2a by way of the second annular segments 12a thereof is aligned between the two projections 13 of the second clip part 2b, and the second clip part 2b by way of the second annular segments 12b thereof is aligned between the two shoulders 9a of the first clip part 2a, said clip parts 2a, 2b in this opened assembly rotary position being plug-fitted axially into one another until said clip parts 2a, 2b by way of the planar base plate 7a, 7b thereof bear on one another on the inside, and the openings 8a, 8b of said clip parts 2a, 2b are congruent. The bearing sleeve 3 that is plug-fitted so as to be non-rotatable in the clip part 2a herein is plug-fitted into the opening 8b of the second clip part 2b, on account of which the two clip part 2a, 2b are mounted so as to be mutually rotatable. Subsequently, the two clip parts 2a, 2b for a rotationally plugged fit are rotated in the direction toward the closed end position thereof, on account of which the first annular segments 11a of the first clip part 2a engage in the circumferential grooves 9b of the second clip part 2b, and the two clip parts 2a, 2b are thus axially interconnected, or locked counter to the plug-fitting direction, respectively.

Once the leg spring 4 by way of the spring coil body 15 thereof has been inserted into the bearing sleeve 3 (FIGS. 1a, 1b), the one, first spring leg 16a of the leg spring 4 in the direction of the spring action thereof bears on the protrusion 14 of the bearing sleeve 3 and is advantageously welded to the protrusion 14. To this end, the height H of the protrusion 14 is preferably larger than the diameter of the spring legs. In other words, the spring leg 16a is supported on an end face 21 of the protrusion 14 facing in the force direction of the leg spring 4 or in the rotation direction of the clip 1, respectively. The other, second spring leg 16b, in a manner similar to that of a clothes peg, encompasses the operating arm 6b of the second clip part 2b; alternatively however, the second spring leg 16b can also be welded to the second clip part 2b. On account of the leg spring 4, the two clip parts 2a, 2b are pretensioned to the closed initial rotary position thereof, on the one hand, and the bearing sleeve 3 is captively held in the clip 1, on the other hand. Instead of plug-fitting the leg spring 4 into the bearing sleeve 3 only once the latter has already been inserted into the first clip part 2a, the leg spring 4 can also be inserted into the bearing sleeve 3 prior to the bearing sleeve 3 being plug-fitted into the first clip part 2a, and said leg spring 4 by way of the first spring leg 16a thereof can be welded to the protrusion 14.

Figure 6A:
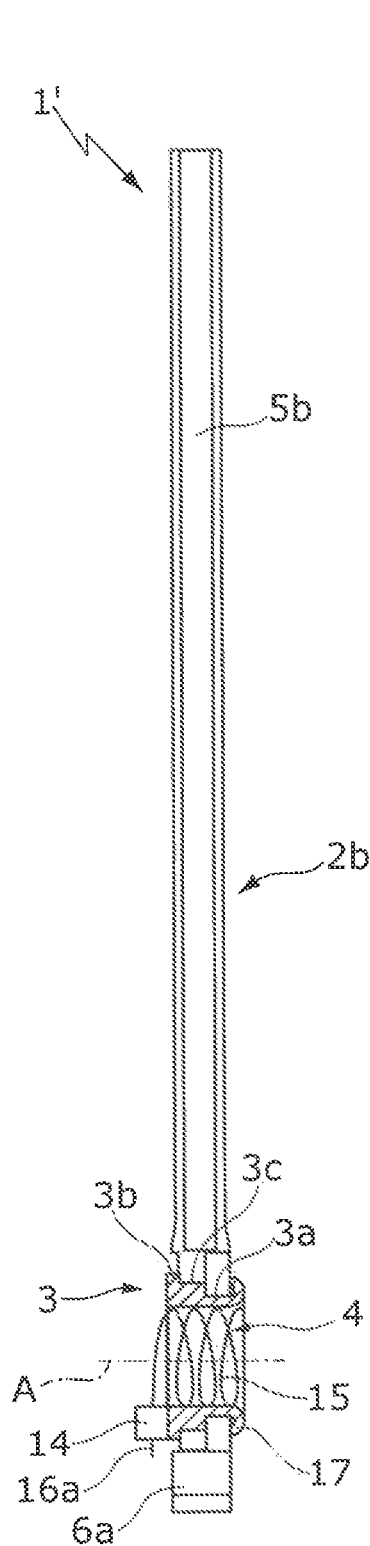
FIGS. 6a, 6b show a second embodiment of the clip according to the invention, said clip being plugged together from two clip parts and one bearing sleeve, in a closed initial rotary position, in a sectional view (FIG. 6a) and in a plan view (FIG. 6b)
Figure 6B:
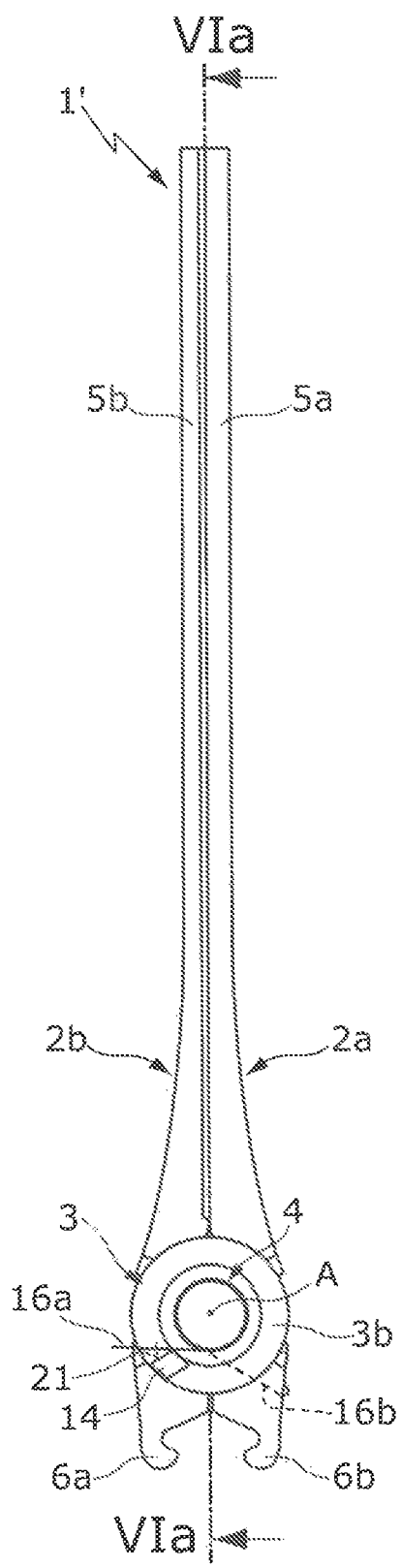

The clip 1 shown in FIGS. 6a, 6b differs from the clip of FIG. 1 only in that the two clip parts 2a, 2b are not interconnected by way of a rotationally plugged fit, but by bending back the bearing sleeve 3. The first clip part 2a shown in FIGS. 7a, 7b is configured in a manner identical to that of the clip part 2a of FIGS. 2a, 2b, and the second clip part 2b shown in FIGS. 8a, 8b, with the exception of the missing projections 13, is configured in a manner identical to that of the clip part 2b of FIGS. 3a, 3b. The bearing sleeve 3 shown in FIGS. 9a, 9b differs from the bearing sleeve shown in FIG. 5 only by way of a longer bearing portion 3a. FIG. 10 finally shows the first clip part 2a having the bearing sleeve 3 plug-fitted so as to be non-rotatable therein.

The first clip part 2a, having the bearing sleeve 3 plug fitted, and the second clip part 2b are assembled like the clip 1 shown in FIG. 1 and are pretensioned by means of the leg spring 4. The bearing sleeve 3 thus forms the rotary mounting about which the second clip part 2b rotates. That end of the longer bearing portion 14b of the bearing sleeve 3 that projects beyond the external side of the second clip part 2b is bent back towards the outside to form a rivet head 17 (FIG. 6a) in order for the two clip parts 2a, 2b to be fastened to one another, or to be axially held together, respectively.

The first clip part 2a shown in FIGS. 11a, 11b differs from the first clip part of FIG. 7 only in that the opening 8a is configured so as to be circular and on the outside has an additional radial recess 18. The second clip part 2b shown in FIGS. 12a, 12b, with the exception of the missing recess, is configured so as to be of a construction identical to that of the first clip part 2a. The bearing sleeve 3' shown in FIGS. 13a, 13b differs from the bearing sleeve 3 of FIG. 9 only in that no octagonal plug portion is present, but instead a protrusion 19 is present on the outside on the bearing portion 3a. The bearing sleeve 3' that is plug-fitted into the first clip part 2a by way of the protrusion 19 of said bearing sleeve 3' engages in the recess 18 of the opening 8a and is thus held so as to be non-rotatable in the opening 8a. The first clip part 2a having the plug-fitted bearing sleeve 3', and the second clip part 2b, are assembled like the clip 1 shown in FIG. 6 and are pretensioned by means of the leg spring 4. The bearing sleeve 3 thus forms the rotary mounting about which the second clip part 2b rotates and axially holds together the two clip parts 2a, 2b between the outer edge 3a thereof and the rivet head 17 thereof.

As is shown in FIG. 14, the protrusion 14 of the bearing sleeve 3, 3' can be configured so as to be hook-shaped, having a projection 20 and thus having a groove 111911 into which the first spring leg 16a is placed and, being axially overreached, is axially fixed. Here, the groove base forms an end face 21 of the protrusion 20 facing in the force direction of the leg spring 4 or in the rotation direction of the clip 1, respectively, for supporting the spring leg 16a.

What is claimed is:

1. A surgical clip, comprising:
   two clip parts that are rotatably interconnected by a separate bearing sleeve; and
   a leg spring which pretensions the two clip parts to an initial rotary position, the leg spring having a coil body and two spring legs;
   wherein the coil body of said leg spring is at least partially disposed within the bearing sleeve;
   wherein the bearing sleeve is disposed so as to be non-rotatable in an opening of a first of the two clip parts and is disposed so as to be rotatable in an opening of a second of the two clip parts; and
   wherein a first of the two spring legs of the leg spring is abuttingly supported on the bearing sleeve, and a second of the two spring legs is supported on the second clip part;
   wherein the bearing sleeve has an encircling outer edge larger than the openings of the first and second of the two clip parts, the encircling outer edge having a non-annular protrusion which protrudes outwards from one of the two clip parts in a direction of an axis of rotation of the two clip parts, and wherein the first spring leg abuts the non-angular protrusion in a rotational direction about the axis of rotation, and wherein the first spring leg is abuttingly supported in the force direction of the leg spring.

2. The surgical clip according to claim 1, wherein the first spring leg is welded, adhesively bonded, or soldered to the non-angular protrusion.

3. The surgical clip according to claim 1, wherein the first spring leg is at least partially embedded in a form-fitting manner in the non-angular protrusion.

4. The surgical clip according to claim 1, wherein an axial height of the non-angular protrusion, the axial height being a distance from an outermost surface of the encircling outer edge to an outermost surface of the non-angular protrusion taken along the direction of the axis of rotation of the two clip parts, is taller than the diameter of the first spring leg.

5. The surgical clip according to claim 1, wherein the non-angular protrusion is configured so as to be hook-shaped and engages radially across the first spring leg.

6. The surgical clip according to claim 1, wherein the radial thickness of the non-angular protrusion is thicker than a wall thickness of a bearing portion of the bearing sleeve on which the second clip part is rotatably mounted.

7. The surgical clip according to claim 1, wherein an axial height of the non-angular protrusion, the axial height being a distance from an outermost surface of the encircling outer edge to an outermost surface of the non-angular protrusion taken along the direction of the axis of rotation of the two clip parts, is taller than a height of the encircling outer edge of the bearing sleeve, the height being a distance from the outermost surface of the encircling outer edge to an innermost surface of the encircling outer edge.

8. The surgical clip according to claim 1, wherein a sleeve end is bent back so as to form a rivet head.

9. The surgical clip according to claim 1, wherein the bearing sleeve has a plug-in portion which has a non-circular external cross section and which is plug-fitted so as to be non-rotatable in that opening of the first clip part that is configured so as to be non-circular.

10. The surgical clip according to claim 1, wherein the two clip parts have each one clamping arm, one operating arm, and one middle portion located therebetween, said middle portion having the openings.

11. The surgical clip according to claim 1, wherein the second spring leg of the leg spring is hooked onto the second clip part.

12. The surgical clip according to claim 1, wherein the second spring leg of the leg spring is welded, adhesively bonded, or soldered to the second clip part.

13. The surgical clip according to claim 1, wherein the bearing sleeve and/or the leg spring are/is formed from a metal.

14. The surgical clip according to claim 1, wherein the two clip parts are formed from a plastics material.

15. The surgical clip according to claim 1, wherein the surgical clip is an aneurysm surgical clip.

16. The surgical clip according to claim 1, wherein the bearing sleeve and the leg spring are formed from a metal, and wherein the two clip parts are formed from a plastics material.

17. The surgical clip according to claim 16, wherein the bearing sleeve is formed from titanium and the two clip parts are formed from PEEK.

18. The surgical clip accordingly to claim 1, wherein the leg spring is not welded to the bearing sleeve.

19. A surgical clip, comprising:
two clip parts that are rotatably interconnected by a separate bearing sleeve, the bearing sleeve defining a sleeve axis; and
a leg spring which pretensions the two clip parts to an initial rotary position, the leg spring having a coil body and two spring legs;
wherein the coil body of said leg spring is at least partially disposed within the bearing sleeve;
wherein the bearing sleeve is disposed so as to be non-rotatable in an opening of a first of the two clip parts and is disposed so as to be rotatable in an opening of a second of the two clip parts; and
wherein a first of the two spring legs of the leg spring is supported on the bearing sleeve, and a second of the two spring legs is supported on the second clip part;
wherein the bearing sleeve has a plug-in portion which has a non-circular external cross section and which is plug-fitted so as to be non-rotatable in the opening of the first clip part that is configured so as to be non-circular;
wherein the bearing sleeve has an encircling annular collar which adjoins on the plug-in portion in the direction of the sleeve axis and the outer diameter of which is greater than the outer diameter of the plug-n portion;
wherein the bearing sleeve has a non-angular protrusion which protrudes outwards from the encircling annular collar in the direction of the sleeve axis, and wherein the first spring leg abuts on the non-angular protrusion in the circumferential direction of the bearing sleeve and is abuttingly supported in the force direction of the leg spring.

* * * * *